US012570947B2

(12) United States Patent (10) Patent No.: US 12,570,947 B2
Park et al. (45) Date of Patent: Mar. 10, 2026

(54) BUFFER PREPARATION AND TRANSFER SYSTEM FOR ANTIBODY DRUG MANUFACTURING PROCESS

(71) Applicant: PRESTIGE BIOLOGICS CO., LTD., Chungcheongbuk-do (KR)

(72) Inventors: Joo Yang Park, Seoul (KR); Ja Won Shin, Sejong (KR); Dae Yang Oh, Seoul (KR)

(73) Assignee: PRESTIGE BIOLOGICS CO., LTD., Cheongju-si (KR)

( * ) Notice: Subject to any disclaimer, the term of this patent is extended or adjusted under 35 U.S.C. 154(b) by 782 days.

(21) Appl. No.: 17/910,596

(22) PCT Filed: Mar. 8, 2021

(86) PCT No.: PCT/KR2021/002839
§ 371 (c)(1),
(2) Date: Sep. 9, 2022

(87) PCT Pub. No.: WO2021/194128
PCT Pub. Date: Sep. 30, 2021

(65) Prior Publication Data
US 2023/0134735 A1 May 4, 2023

(30) Foreign Application Priority Data
Mar. 23, 2020 (KR) ........................ 10-2020-0035279

(51) Int. Cl.
*C12M 1/34* (2006.01)
*C07K 1/18* (2006.01)
*C12M 1/00* (2006.01)

(52) U.S. Cl.
CPC .............. *C12M 41/32* (2013.01); *C07K 1/18* (2013.01); *C12M 23/28* (2013.01); *C12M 29/00* (2013.01); *C12M 47/10* (2013.01)

(58) Field of Classification Search
None
See application file for complete search history.

(56) References Cited

U.S. PATENT DOCUMENTS

| | | | |
|---|---|---|---|
| 4,116,046 A | 9/1978 | Stein | |
| 2013/0164400 A1 | 6/2013 | Knopov | |
| 2016/0347823 A1 | 12/2016 | Bergmann | |
| 2018/0037861 A1* | 2/2018 | Wilkins | ................ C12M 37/00 |

FOREIGN PATENT DOCUMENTS

| | | |
|---|---|---|
| CN | 104906144 A | 9/2015 |
| JP | 2004-28690 A | 1/2004 |
| JP | 2018-507103 A | 3/2018 |
| KR | 10-2018-0047404 A | 5/2018 |
| KR | 10-2019-0037288 A | 4/2019 |
| WO | 2019158906 A1 | 8/2019 |

OTHER PUBLICATIONS

Office Action from corresponding Korean Patent Application No. 10-2020-0035279, dated Aug. 23, 2021.
Gronemeyer, P., et al.; "Trends in Upstream and Downstream Process Development for Antibody Manufacturing", Bioengineering 2014, 1, 188-212; doi:10.3390/bioengineering1040188.
Extended European Search Report for EP 21774764.1 dated Mar. 28, 2024.
Korean Office Action issued for Korean Patent Application No. 10-2020-0035279 mailed on Mar. 18, 2022.
International Search Report from corresponding PCT Application No. PCT/KR2021/002839, dated Jun. 25, 2021.

* cited by examiner

*Primary Examiner* — Ann Montgomery
(74) *Attorney, Agent, or Firm* — Dinsmore & Shohl LLP; Yongsok Choi, Esq.

(57) ABSTRACT

The present invention provides a buffer preparation and transfer system for a process of manufacturing an antibody pharmaceutical which can reduce the input of a lot of labor due to the preparation of each buffer, including the weighing of a buffer chemical, the input of a powder, stirring and transfer, and significantly shorten process time by positioning and designing components in a manner that automates the preparation and transfer of various buffer solutions using a control unit and controls the concentration and composition of a buffer by transferring a concentrated component solution into the buffer storage tank using an opening/closing valve and a flow rate-adjusting valve, and unlike the related art, reduces the number of buffer preparation tanks corresponding to individual buffer storage tanks, which is advantageous for securing a safe distance between processes and securing a facility area.

4 Claims, 4 Drawing Sheets

BUFFER PREPARATION AND TRANSFER SYSTEM FOR ANTIBODY DRUG MANUFACTURING PROCESS

CROSS-REFERENCE TO RELATED APPLICATIONS

This application is a National Phase application of PCT Application No. PCT/KR2021/002839, filed on 8 Mar. 2021, which claims priority to Korean Patent Application No. 10-2020-0035279, filed on 23 Mar. 2020. The entire disclosures of the applications identified in this paragraph are incorporated herein by reference.

TECHNICAL FIELD

The present invention relates to a buffer preparation and transfer system for a process of manufacturing an antibody pharmaceutical.

BACKGROUND ART

Biopharmaceuticals can be broadly classified into new biologics, improved biopharmaceuticals (biobetters) and biosimilars, and compared with chemically synthesized pharmaceuticals, have fewer side effects and less preclinical data required in research and development, and are easier to predict product efficacy and safety and due to the relatively high probability of clinical success, active development of technology is progressing worldwide.

The process of manufacturing biopharmaceuticals consists of initial candidate material and cell line development, a culture process (upstream processing (USP)), a purification process (downstream processing (DSP)), and a fill and finish process, and particularly, in the case of biosimilar product production, processing optimization in the culture process (USP) and purification process (DSP) is directly related to cost competitiveness, so interest in optimizing the process of manufacturing biosimilars with low cost, high purity and high yield is growing.

In this process, the culture process (USP) corresponds to the process of continuously increasing the number of cells through cell division for approximately 6 weeks from the initial flask stage of less than 1 liter to the final production bioreactor stage of 15,000 L or more, after thawing the cell line, and culture methods that can be used herein include batch culture, fed-batch culture, continuous culture, and perfusion culture and the like.

In addition, the purification process (DSP) is the process of extracting a protein to be used as a pharmaceutical with high purity and high efficiency from the culture in which cells and cell debris are mixed through the manipulation and use of various types of chromatographs and filters, and during the purification process (DSP), column purification, virus removal and ultra/diafiltration are performed through the use of a chromatograph and filters.

Meanwhile, components and systems used in the USP and DSP are divided into stainless steel (SS) and single-use (SU) using disposable bags or tubes in terms of material, and among these, although the SS process system including device components made of SS has advantages of easy implementation on a relatively large scale, low operation cost and easy automation, the initial installation cost is high, it is vulnerable to contamination and prone to the downstream bottleneck phenomenon occurring in the DSP, caused by the implementation of a large-sized bioreactor.

The SU process system, which has recently been introduced, uses disposable bags or tubes with a volume of 0.1 to 2,000 L as device components, and compared to the SS process system, has advantages of relatively low cost for initial installation and being relatively resistant to contamination because a corresponding part can be replaced upon contamination. However, scale-up limitations, continuous operation costs caused by frequent bag replacement and the input of a lot of labor during equipment replacement are pointed out as disadvantages.

In the field of biopharma today, there are more and more companies serving as contract manufacturing organizations (CMOs) for drugs for clinical trials and commercial use, and furthermore, improvement in one-stop service from cell line development and related process development, scale-up to commercial production is also made.

Meanwhile, the purification process essentially includes a chromatography process using the characteristic (surface charge or hydrophobicity) of a protein molecule to remove impurifies and obtain a high purity antibody, and here, various buffer solutions are used. The conventional buffer preparation process used a system in which buffers are prepared manually one by one and a buffer preparation tank and a buffer storage tank are matched in a 1:1 ratio, and used to assist a device for preparing a buffer by diluting a concentrated buffer solution. According to the related art, a large facility area is required for tank instillation, and since the buffer was prepared manually, there was a problem in that a lot of labor and time were invested. In addition, there was a problem in that chemicals are blown out during powder work for preparing a buffer, which adversely affects the health of workers.

DISCLOSURE

Technical Problem

In view of the above problems, the present invention is directed to providing a buffer preparation and transfer system for a process of manufacturing an antibody pharmaceutical, which can reduce the input of a lot of labor due to the preparation of each buffer, including the weighing of a buffer chemical, the input of a powder, stirring and transfer, and significantly shorten process time by positioning and designing components in a manner that automates the preparation and transfer of various buffer solutions using a control unit and controls the concentration and composition of a buffer by transferring a concentrated component solution into the buffer storage tank using an opening/closing valve and a flow rate-adjusting valve, unlike a conventional buffer preparation process using a system in which buffers are prepared manually one by one and a buffer preparation tank and a buffer storage tank are matched in a 1:1 ratio.

In addition, technical problems to be solved in the present invention are not limited to the above-described technical problems, and other problems which are not described herein will be fully understood by those of ordinary skill in the art from the following descriptions.

Technical Solution

The specification provides a buffer preparation and transfer system for a process of manufacturing an antibody pharmaceutical, which includes: one or more concentrated component tanks receiving a concentrated component solution from a buffer preparation tank; a first pipeline connected with a first discharge line along which the concentrated component solution is discharged from concentrated component tank; one or more buffer storage tanks having concentrated component input lines each branched from the first pipeline and positioned in parallel; a second pipeline connected with the second discharge line along which a buffer is discharged from each buffer storage tank; a chromatograph connected with the second pipeline; and a control unit, wherein the control unit transfers the concentrated component solution to each buffer storage tank by adjusting the opening/closing of an opening/closing valve located on the first discharge line of each concentrated component tank or adjusting a flow rate with a flow rate-adjusting valve located on the concentrated component input line through which a concentrated component is introduced into each buffer storage tank, based on a predetermined value.

In addition, in the specification, a line for injecting water for injection is connected to each buffer storage tank, and the buffer storage tank batch-conditions the injected concentrated component solution and the water for injection.

In addition, in the specification, by comparing the values measured from one or more sensors selected from a weight sensor, a conductivity sensor, and a pH sensor provided in each buffer storage tank with a predetermined reference value, the control unit controls the concentration and composition of a buffer in each buffer storage tank by adjusting the opening/closing of the opening/closing valve located on the first discharge line of each concentrated component tank or adjusting a flow rate with the flow rate-adjusting valve located on the concentrated component input line through which the concentrated component solution is introduced to each buffer storage tank.

In addition, in the specification, the opening/closing valve is a pinch valve, and the flow rate-adjusting valve is a diaphragm valve.

In addition, in the specification, the concentrated component tank is formed of a single-use (SU) disposable bag, and the buffer storage tank is formed of a stainless steel (SS) material.

In addition, in the specification, the chromatograph of the purification unit may be one selected from an affinity chromatograph, an ion exchange chromatograph, a hydrophobic interaction chromatograph and a mixed-mode chromatograph, or a combination thereof.

In addition, in the specification, the buffer preparation and transfer system may be applied to prepare and transfer a buffer for a process of purifying one or more antibody pharmaceuticals selected from the group consisting of abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, ustekinumab, visilizumab, votumumab, zalutumumab, brodalumab, anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, adornase alfa, Rebif, becaplermin, alteplase, laronidase, alefacept, aflibercept, raxibacumab, darbepoetin alfa, becaplermin concentrate, interferon beta-1b, botulinum toxin type A, rasburicase, asparaginase, epoetin alfa, etanercept, agalsidase beta, interferon alfacon-1, interferon alfa-2a, anakinra, botulinum toxin type B, pegfilgrastim, oprelvekin, filgrastim, denileukin diftitox, peginterferon alfa-2a, aldesleukin, dornase alfa, interferon beta-1a, becaplermin, reteplase, interferon alfa-2, tenecteplase, drotrecogin alfa, rilonacept, romiplostim, methoxypolyethylene glycol-epoetin beta, a C1 esterase inhibitor, idursulfase, alglucosidase alfa, abatacept, galsulfase, palifermin and interferon gamma-1b.

Advantageous Effects

A buffer preparation and transfer system according to the present invention can reduce the input of a lot of labor due to the preparation of each buffer, including the weighing of a buffer chemical, the input of a powder, stirring and transfer, and significantly shorten process time by positioning and designing components in a manner that automates the preparation and transfer of various buffer solutions using a control unit and controls the concentration and composition of a buffer by transferring a concentrated component solution into the buffer storage tank using an opening/closing valve and a flow rate-adjusting valve, unlike a conventional buffer preparation process using a system in which buffers are prepared manually one by one and a buffer preparation tank and a buffer storage tank are matched in a 1:1 ratio.

In addition, unlike the related art, the buffer preparation and transfer system of the present invention reduces the number of buffer preparation tanks corresponding to individual buffer storage tanks, which is advantageous for securing a safe distance between processes and securing a facility area, and it is possible to secure the safety of workers due to the automated system.

In addition, as the buffer preparation tank and the concentrated component tank are formed of a single-use (SU) disposable bag, corrosion (corrosion of a metal by an acid) caused by the use of a high-concentration buffer solution can be minimized, and a separate washing and sterilization process can be omitted, thereby further shortening the process time.

Further, the buffer preparation and transfer system of the present invention has great advantages in that buffer quality is uniform compared to the related art, and the buffer solution can be prepared according to a desired recipe.

MODES OF THE INVENTION

Figure 1:
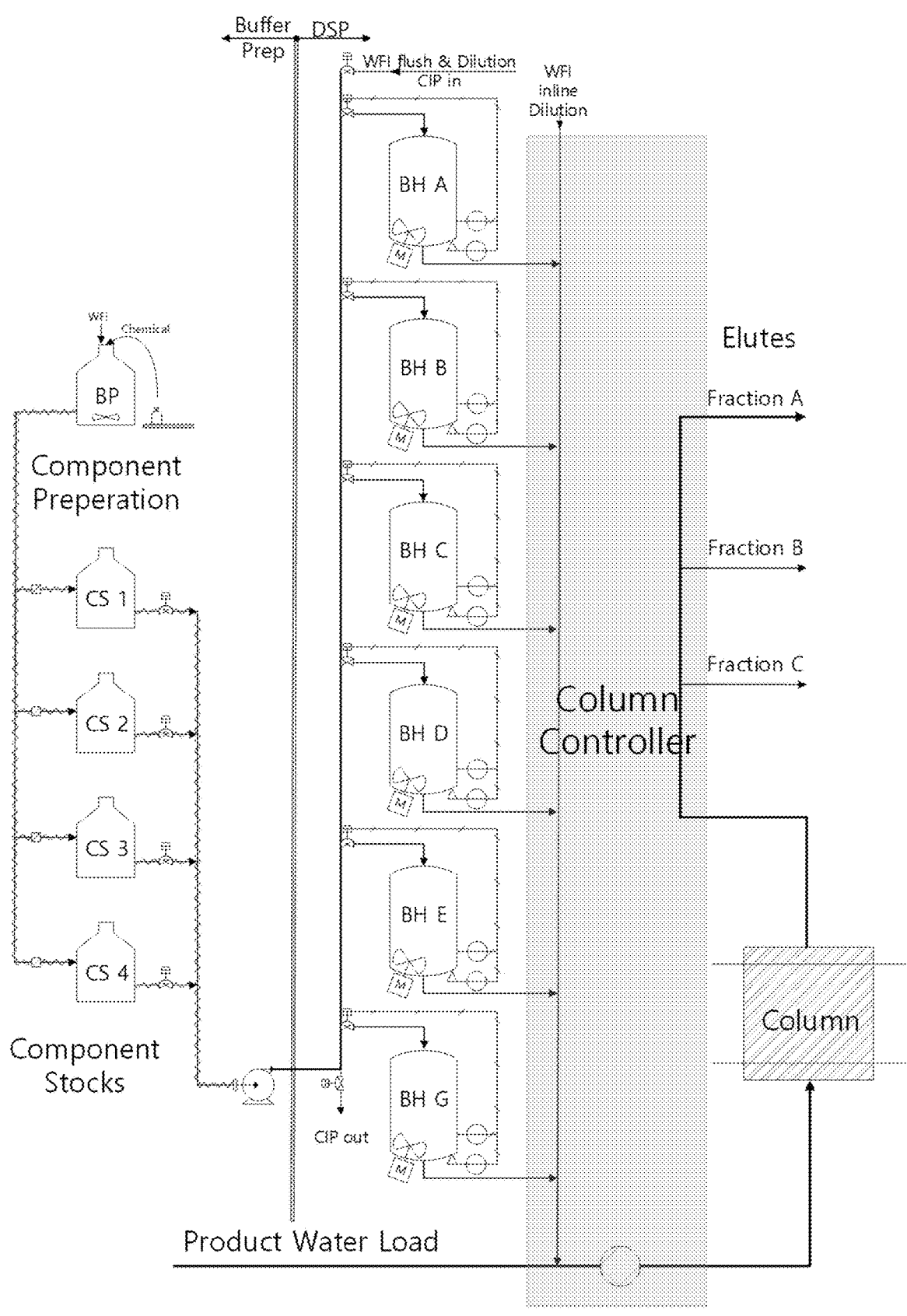
FIG. 1 schematically shows a buffer preparation and transfer system for a process of manufacturing an antibody pharmaceutical implemented according to one embodiment of the present invention.

The terms used in the specification are used only to describe specific examples, not to limit the present invention. Singular expressions include plural expressions unless clearly indicated otherwise in the context. It should be understood that the term "comprise," "include," or "have" used herein is for indicating the presence of implemented characteristics, numbers, steps, elements or a combination thereof, and does not preclude the possibility of the presence or addition of one or more other characteristics, numbers, steps, elements or a combination thereof.

In addition, in the present invention, when a layer or element is referred to as being formed "on" or "over" each layer or element, it is meant that each layer or element is formed directly on each layer or element, or another layer or element is formed on each layer, or that another layer or element may additionally be formed between layers, on an object, or a substrate.

The present invention may have various modifications and various examples, and thus specific examples are illustrated in the drawings and described in detail in the detailed description. However, it should be understood that the present invention is not limited to specific embodiments, and includes all modifications, equivalents or alternatives within the spirit and technical scope of the present invention.

Meanwhile, the term "component" used throughout the specification and claims of the present invention should be understood to mean an individual component of a buffer solution.

In addition, in the present invention, the term "unit" used throughout the specification and claims may mean a software or hardware component, and the "unit" performs a certain role. However, the "unit" is not limited to software or hardware. The "unit" may be configured to be present in an addressable storage medium or to regenerate one or more processors. Therefore, in one example, the "unit" includes components such as software components, object-oriented software components, class components and task components, processors, functions, properties, procedures, subroutines, segments of program code, drivers, firmware, microcode, circuit, data, database, data structures, tables, arrays, and variables. The functions provided in the components and "units" may be combined into a smaller number of components and "units," or further separated into additional components and "units."

According to one embodiment of the present invention, the "unit" may be implemented as a processor and a memory. The term "processor" should be construed broadly to include a general-purpose processor, a central processing unit (CPU), a microprocessor, a digital signal processor (DSP), a controller, a microcontroller, and a state machine. In some circumstances, the "processor" may refer to an application-specific integrated circuit (ASIC), a programmable logic device (PLD), or a field programmable gate array (FPGA). The term "processor" may also refer to a combination of processing devices, for example, a combination of a DSP and a microprocessor, a combination of a plurality of microprocessors, a combination of one or more microprocessors combined with a DSP core, or a combination of random components.

The term "memory" should be construed broadly to include any electronic component that can store electronic information. The term "memory" may also refer to various types of processor-readable media such as a random access memory (RAM), a read-only memory (ROM), a non-volatile random access memory (NVRAM), a programmable read-only memory (PROM), an erase-programmable read-only memory (EPROM), an electrically erasable PROM (EE-PROM), a flash memory, magnetic or optical data storage devices, and registers. A memory is said to be in electronic communication with the processor if the processor is capable of reading information from and/or writing information to the memory. The memory integrated in the processor is in electronic communication with the processor.

Hereinafter, buffer preparation and transfer system for a process of manufacturing an antibody pharmaceutical according to exemplary embodiments of the present invention will be described in further detail.

Buffer Preparation and Transfer System for a Process of Manufacturing an Antibody Pharmaceutical A buffer preparation and transfer system for a process of manufacturing an antibody pharmaceutical according to one embodiment of the present invention includes one or more concentrated component tanks receiving a concentrated component solution from a buffer preparation tank; a first pipeline connected with a first discharge line along which the concentrated component solution is discharged from the concentrated component tanks; one or more buffer storage tanks having concentrated component input lines each branched from the first pipeline and positioned in parallel; a second pipeline connected with a second discharge line along which a buffer is discharged from each buffer storage tank; a chromatograph connected with the second pipeline; and a control unit, wherein the control unit transfers the concentrated component solution to each buffer storage tank by adjusting the opening/closing of an opening/closing valve located on the first discharge line of each concentrated component tank, or adjusting a flow rate with a flow rate-adjusting valve located on the concentrated component input line through which a concentrated component is introduced into each buffer storage tank, based on a predetermined value.

In further detail, the process of manufacturing antibody pharmaceuticals consists of initial candidate material and cell line development, a culture process (upstream processing (USP)), a purification process (downstream processing (DSP)), and a fill and finish process.

In these processes, the purification process corresponds to a process of extracting a protein to be used as a pharmaceutical with high purity and high efficiency from the culture in which cells and cell debris are mixed through the manipulation and use of various types of chromatographs and filters.

The purification unit according to one embodiment of the present invention is a set of components for the culture process, which may include a buffer preparation tank for preparing a buffer in advance; a buffer storage tank for receiving the buffer from the buffer preparation tank and storing the buffer; a chromatograph increasing the purity of a target protein by removing the impurities mixed in the culture medium using the culture medium received from the culture process and the buffer received from the buffer storage tank; and one or more filtration systems disposed before or after chromatography to perform buffer exchange and concentration.

One or more concentrated component tanks that store the concentrated component solution may be provided between the buffer preparation tank and the buffer storage tank.

Meanwhile, the purification process essentially includes a chromatography process using the characteristic (surface charge or hydrophobicity) of a protein molecule to remove impurities and obtain a high purity antibody, and various buffer solutions are used. In the conventional buffer preparation process, a system in which buffers are prepared manually one by one and a buffer preparation tank and a buffer storage tank are matched in a 1:1 ratio was used and used to assist a device for preparing a buffer by diluting a concentrated buffer solution. According to the related art, a large facility area is required for tank instillation, and since the buffer was prepared manually, there was a problem in that a lot of labor and time were invested. In addition, there was a problem in that chemicals are blown out during powder work for preparing a buffer, which adversely affects the health of workers.

The present inventors confirmed that, unlike a conventional buffer preparation process using a system in which buffers are prepared manually one by one and a buffer preparation tank and a buffer storage tank are matched in a 1:1 ratio, when components are positioned and designed in a manner that automates the preparation and transfer of various buffer solutions using a control unit and the concentration and composition of a buffer are controlled by transferring a concentrated component solution into the buffer storage tank using an opening/closing valve and a flow rate-adjusting valve, and a buffer preparation tank and a concentrated component tank are formed of a single-use (SU) disposable bag, the input of a lot of labor due to the preparation of each buffer, including the weighing of a buffer chemical, the input of a powder, stirring and transfer can be reduced, process time can be significantly shortened, corrosion (corrosion of a metal by an acid) caused by the use of a high-concentration buffer solution can be minimized, and a separate washing and sterilization process can be omitted, thereby further shortening the process time, and completed the present invention.

Specifically, according to one embodiment of the present invention, one or more concentrated component tanks receiving the concentrated component solution from the buffer preparation tank formulating each component of a buffer solution used to stably extract a protein as a liquid buffer and an acidity regulator may be included, and a buffer storage tank sending components of the concentrated component solution and water for injection to the chromatograph from the concentrated component tank after conditioning may be included. Meanwhile, the concentrated component tank is connected with one or more buffer storage tanks through a first pipeline to which a first discharge line for discharging the concentrated component solution is connected and a concentrated component input line branched from the first pipeline. Meanwhile, an opening/closing valve is located on the first discharge line, and a flow rate-adjusting valve is located on the concentrated component input line. Meanwhile, a second discharge line discharged from each buffer storage tank is connected with a second pipeline, and the second pipeline is connected with the chromatograph (see FIG. 1). Meanwhile, to prepare a desired buffer solution, the one or more concentrated component tanks may include an individual component constituting the buffer solution, and in one example, the one or more concentrated component tanks may include different buffer components.

Meanwhile, as the components of the buffer preparation and transfer system according to one embodiment of the present invention, a buffer preparation tank, a concentrated component tank, a buffer storage tank, a first discharge line, a first pipeline, a second discharge line, a second pipeline and a chromatograph may be made of one or more materials selected from a stainless steel (SS) material and an SU disposable bag, and for example, the system may be a hybrid system in which the SS material and the SU disposable bag are mixed.

Meanwhile, in the present invention, the buffer preparation tank and the one or more concentrated component tanks may be disposable bags, and when the buffer preparation tank and the concentrated component tank are made of the above-described material, compared to the conventional components formed of SS materials, the risk of corrosion (metal corrosion caused by an acid) according to the use of a high-concentration component is minimized, the difficulty in washing and sterilization is reduced, and since it is possible to transition to a new process with simple replacement, it has the effect of shortening the process time. Meanwhile, the term "single-use (SU) disposable bag" used throughout the specification and claims may be a concept encompassing an SU disposable bag as well as a washable plastic bottle configuration.

In addition, since the buffer preparation and transfer system according to the present invention uses a highly-concentrated component solution, it is possible to reduce a size by $\frac{1}{25}$ compared to the standard buffer preparation tank, and the buffer storage tank also receives a concentrated component and then controls the concentration with water for injection immediately before the injection into the chromatograph, so it is possible to reduce the burden of storing the buffer solution and accordingly reduce a size by $\frac{1}{10}$ compared to the existing buffer storage tank.

Meanwhile, a line for injecting water for injection is connected to each buffer storage tank according to one embodiment of the present invention, and the buffer storage tank is capable of batch conditioning an injected concentrated component solution and water for injection. Meanwhile, the water for injection may be mixed with one or more concentrated component solutions injected into the buffer storage tank and thus adjust the concentration of the buffer solution. Meanwhile, the flow rate(s) of one or more component solutions may be adjusted by a control unit, and then the component solutions may be injected into the buffer storage tank to prepare a desired buffer solution.

Meanwhile, the buffer preparation and transfer system according to one embodiment of the present invention includes a control unit.

The control unit may be a component for controlling the concentration and composition of a buffer in each buffer storage tank by adjusting the opening/closing of an opening/closing valve located on the first discharge line of each concentrated component tank or adjusting a flow rate with a flow rate-adjusting valve located on the concentrated component input line through which the concentrated component solution is introduced to each buffer storage tank, comparing the values measured from one or more sensors selected from a weight sensor, a conductivity sensor, and a pH sensor provided in each buffer storage tank with a predetermined reference value.

Specifically, the control unit may include one or more components selected from a processor and a memory, and in the processor, instructions stored in the memory may be executed. Meanwhile, the processor may include, for example, a central processing unit (CPU), a graphics processing device (GPU) or both, and in one example, may be of a type in which the process operation is automated (adjusted and controlled) by the processor and the memory in the control unit.

In one example, the control unit according to one embodiment of the present invention may be a programmable logic controller (PLC). Particularly, when the control unit is a PLC, by comparing the values measured from one or more sensors selected from the weight sensor, conductivity sensor, and pH sensor provided in each buffer storage tank with a predetermined threshold, the opening/closing of an opening/closing valve, for example, a pinch valve, located on the first discharge line of each concentrated component tank, may be adjusted, or the flow rate of a flow rate-adjusting valve, for example, a diaphragm valve, located on the concentrated component input line through which the concentrated component solution is introduced to each buffer storage tank, may be adjusted, thereby controlling the buffer concentration and composition in the buffer storage tank.

Figure 2:
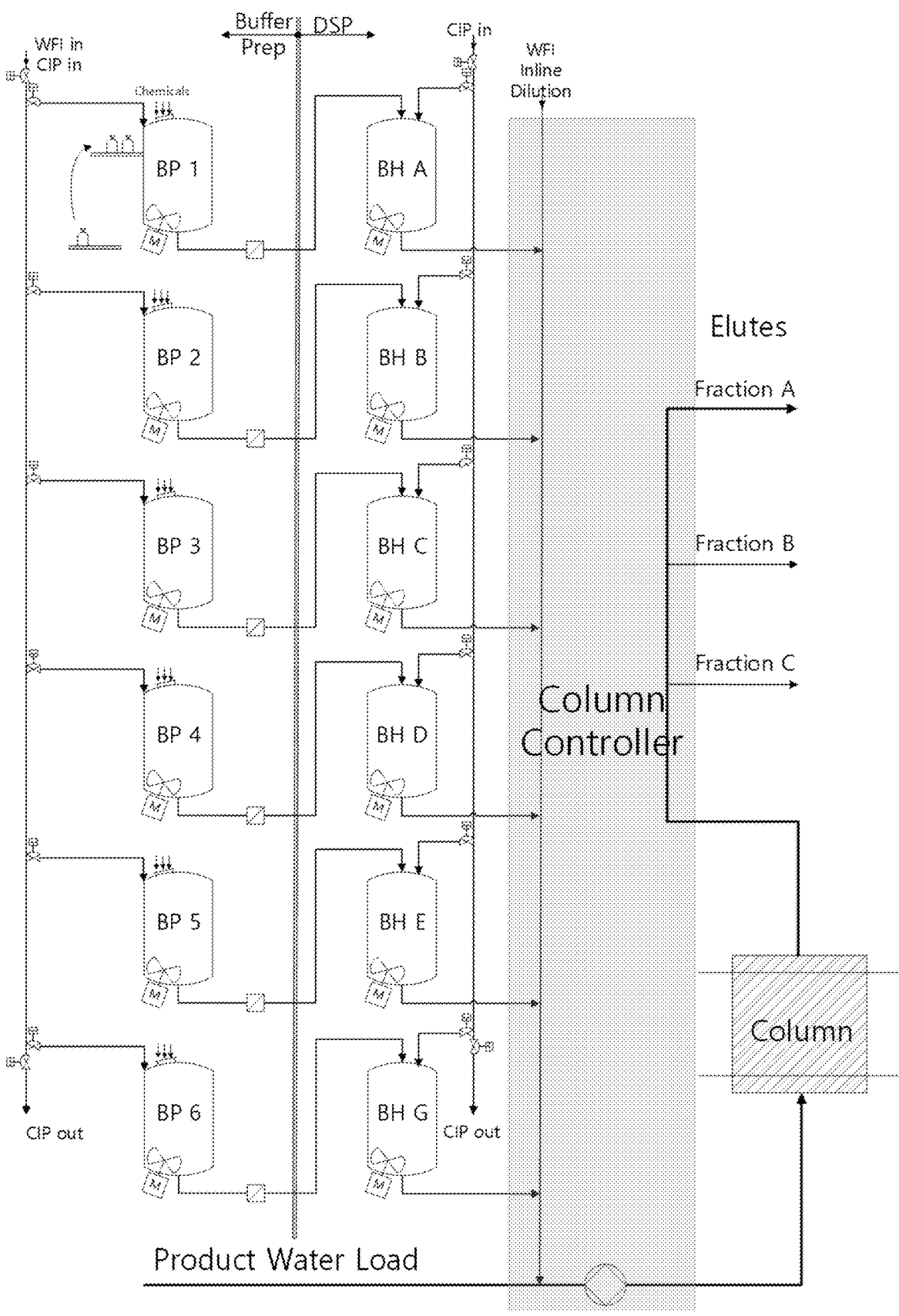
FIG. 2 schematically shows a buffer preparation and transfer system for a process of manufacturing an antibody pharmaceutical according to an example of the related art.

A buffer preparation and transfer method according to the related art is to fill a preparation tank with water for injection (WFI), add quantitatively-weighed buffer component materials, stir the resulting solution, adjust conductivity and pH, check a volume, and then perform fill-up, and after filtration, the entire amount of the buffer prepared in the preparation tank is transferred to the buffer storage tank, and as various types of buffers are used in each step of the purification process, the buffer preparation and transfer had to be repeated (see FIG. 2).

Although there are differences between products and processes, the amount of a buffer input to the purification process during first batch production reaches several times the amount of a medium used in the culture process. In addition, in this method, the buffer preparation tank and the buffer storage tank are matched in a 1:1 ratio, so a large facility is required for individual tank installation, whereas a lot of labor is input and the process time is delayed.

Figure 3:
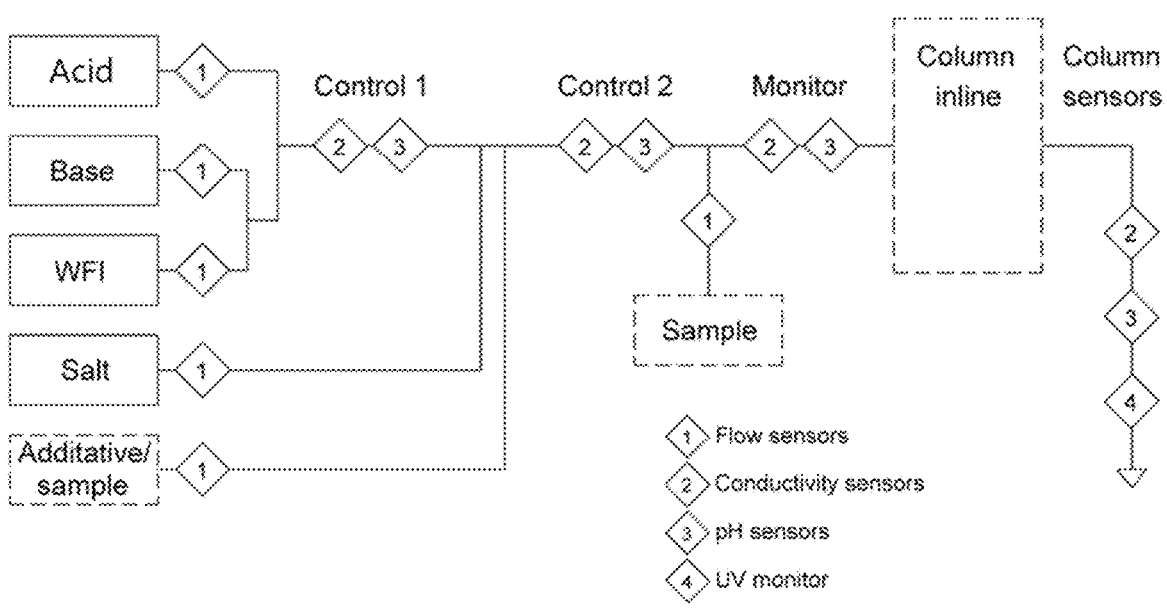
FIG. 3 schematically shows a buffer preparation and transfer system for a process of manufacturing an antibody pharmaceutical according to another example of the related art.

In addition, by the recognition of this problem, equipment (Inline Conditioning System) that mixes concentrated component solutions in a pipeline in a Skid while controlling the input flow rate ratio for each solution in the form of a current Skid and then injects the resulting mixture directly into a column was commercialized, but it is very expensive, and takes a lot of time for validation due to a large variance in buffer quality compared to the traditional method (see FIG. 3).

Figure 4:
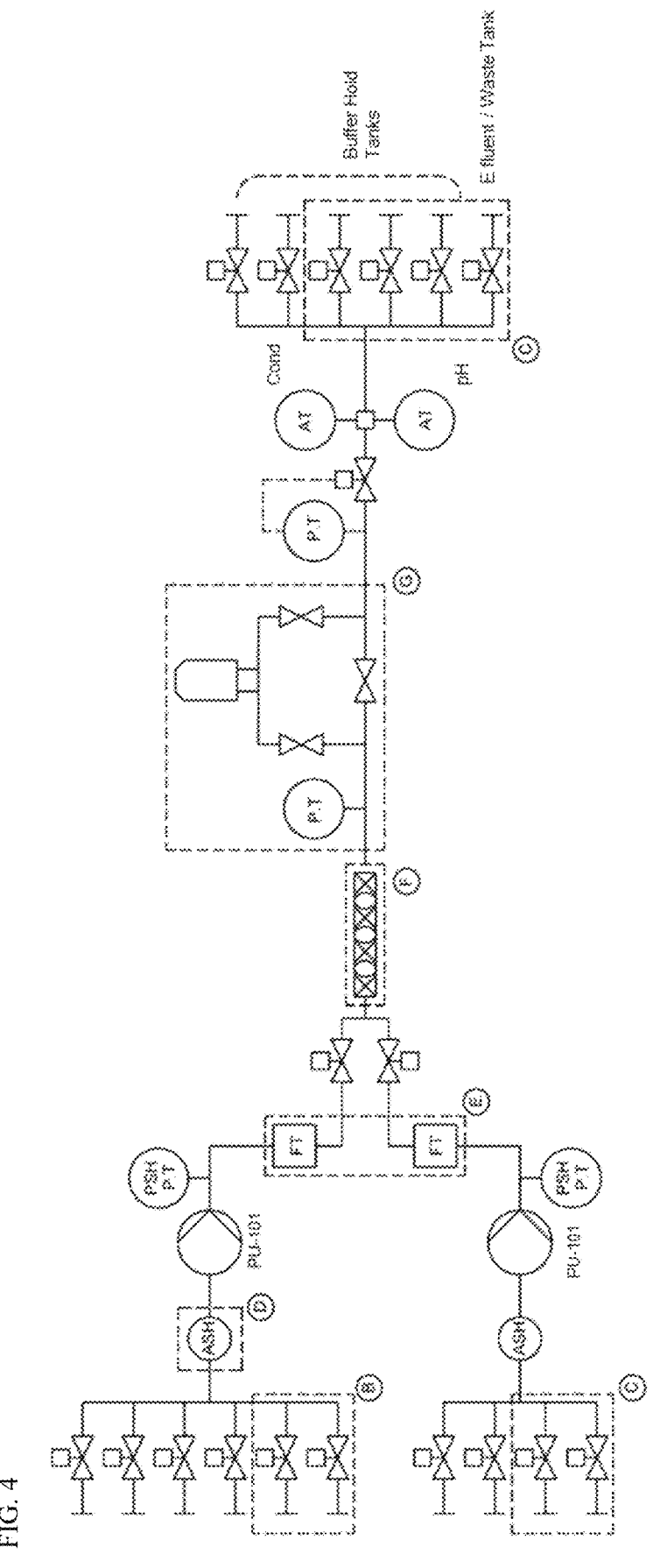
FIG. 4 schematically shows a buffer preparation and transfer system for a process of manufacturing an antibody pharmaceutical according to still another example of the related art.

In addition, another method that has emerged as an alternative to the conventional buffer preparation and transfer method is a method of putting a buffer solution into a buffer storage tank, not a method of putting it directly into a column, and there is a method of controlling a flow rate using several pumps and installing a line mixer for mixing in a transfer line, but it also generates a lot of waste and does not guarantee the same quality as in batch preparation (see FIG. 4).

On the other hand, in the case of the present invention, the control unit is used to automate the preparation and transfer of various buffer solutions, and only by positioning and designing components such that the concentration and composition of a buffer are controlled by transferring the concentrated component solution into the buffer storage tank using the opening/closing valve and the flow rate-adjusting valve, the input of a lot of labor due to the preparation of each buffer, including the weighing of a buffer chemical, the input of a powder, stirring and transfer, may be reduced and the process time may be significantly shortened.

In addition, the buffer preparation and transfer system of the present invention reduces the number of buffer preparation tanks corresponding to individual buffer storage tanks, which is advantageous for securing a safe distance between processes and securing a facility area, and it is possible to secure the safety of workers due to the automated system.

In addition, as the buffer preparation tank and the concentrated component tank are formed of a single-use (SU) disposable bag, corrosion (corrosion of a metal by an acid) caused by the use of a high-concentration buffer solution can be minimized, and a separate washing and sterilization process can be omitted, thereby further shortening the process time. Moreover, compared to the related art, the buffer preparation and transfer system of the present invention great advantages in that buffer quality is uniform compared to the related art, and the buffer solution can be prepared according to a desired recipe.

Meanwhile, the buffer preparation and transfer system according to one embodiment of the present invention may be applied to prepare and transfer a buffer for a process of purifying one or more antibody pharmaceuticals selected from the group consisting of abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, ustekinumab, visilizumab, votumumab, zalutumumab, brodalumab, anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, adornase alfa, Rebif, becaplermin, alteplase, laronidase, alefacept, aflibercept, raxibacumab, darbepoetin alfa, becaplermin concentrate, interferon beta-1b, botulinum toxin type A, rasburicase, asparaginase, epoetin alfa, etanercept, agalsidase beta, interferon alfacon-1, interferon alfa-2a, anakinra, botulinum toxin type B, pegfilgrastim, oprelvekin, filgrastim, denileukin diftitox, peginterferon alfa-2a, aldesleukin, dornase alfa, interferon beta-1a, becaplermin, reteplase, interferon alfa-2, tenecteplase, drotrecogin alfa, rilonacept, romiplostim, methoxypolyethylene glycol-epoetin beta, a C1 esterase inhibitor, idursulfase, alglucosidase alfa, abatacept, galsulfase, palifermin and interferon gamma-1b, and it can be variously used throughout a process of manufacturing antibody pharmaceuticals, such as biopharmaceuticals, improved biopharmaceuticals (biobetters) and biosimilars.

In addition, the system according to the present invention may be effectively used when the components of the buffer solution used for washing and elution in the chromatography (cation exchange, hydrophobic interaction exchange, anion exchange, etc.) process during the process of purifying an antibody pharmaceutical are simplified (for example, when a plurality of buffer solutions are prepared to have two or more components and prepared in a manner that increases only one component). In addition, in this case, the buffer preparation tank does not need to be matched with the buffer storage tank in a 1:1 ratio, so there is an advantageous effect in securing a safe distance between processes and securing the facility area compared to the related art.

In addition, when the buffer preparation and transfer system for a process of manufacturing an antibody pharmaceutical is applied, even if individual buffer solutions are not prepared one by one, various types of buffer solutions can be easily prepared with the automated system.

11

TABLE 1

Composition of CEX buffer and component concentration

| CEX Buffer | Recipe | Component (mM) | | | |
|---|---|---|---|---|---|
| | | NaAc | HAc | NaCl | NaOH |
| A | pH 5, 20 mM NaAc + 40 mM NaCl | 20 | 9 | 40 | |
| B | pH 6, 30 mM NaAc | 30 | 1.5 | | |
| C | pH 6, 30 mM NaAc + 50 mM NaCl | 30 | 2.1 | 50 | |
| D | pH 6, 30 mM NaAc + 80 mM NaCl | 30 | | 80 | |
| E | pH 6, 30 mM NaAc + 110 mM NaCl | 30 | 1.2 | 110 | |
| G | 2000 mM NaCl | | | 2000 | |
| H | 1000 mM NaOH | | | | 1000 |

TABLE 2

Composition of CEX buffer and concentration of alternative component

| CEX Buffer | Recipe | Alternative Component (mM) | | |
|---|---|---|---|---|
| | | HCl | HAc | NaOH |
| A | pH 5, 20 mM NaAc + 40 mM NaCl | 40 | 29 | 60 |
| B | pH 6, 30 mM NaAc | | 31.5 | 30 |
| C | pH 6, 30 mM NaAc + 50 mM NaCl | 50 | 32.1 | 80 |
| D | pH 6, 30 mM NaAc + 80 mM NaCl | 80 | 31.3 | 110 |
| E | pH 6, 30 mM NaAc + 110 mM NaCl | 110 | 31.2 | 140 |
| G | 2000 mM NaCl | 2000 | | 2000 |
| H | 1000 mM NaOH | | | 1000 |

In one example, when the buffer solutions required for cation exchange chromatography are as shown in Tables 1 and 2 above, and are prepared manually according to the related art, a total of seven each of buffer solutions and buffer preparation tanks are needed, and not only the input of a lot of labor due to the preparation of each buffer, including the weighing of a buffer chemical, the input of a powder, stirring and transfer is required, but also the process time significantly increases.

On the other hand, when the concentrated component solution and the control unit according to the present invention are used to inject the concentrated component solution and water for injection into the buffer storage tank at appropriate amounts by an automated process, automated preparation of buffer solutions is possible only by including a total of four component tanks (NaAc, HAc, NaCl and NaOH) in the case of Table 1 and a total of three component tanks (HCl, HAc and NaOH) in the case of Table 2, and thus the economic feasibility and efficiency of the process can be improved.

The buffer preparation and transfer system described above can reduce the input of a lot of labor due to the preparation of each buffer, including the weighing of a buffer chemical, the input of a powder, stirring and transfer, and significantly shorten process time by positioning and designing components in a manner that automates the preparation and transfer of various buffer solutions using a control unit and controls the concentration and composition of a buffer by transferring a concentrated component solution into the buffer storage tank using an opening/closing valve and a flow rate-adjusting valve, unlike a conventional buffer preparation process using a system in which buffers are prepared manually one by one and a buffer preparation tank and a buffer storage tank are matched in a 1:1 ratio.

In addition, unlike the related art, the buffer preparation and transfer system of the present invention reduces the number of buffer preparation tanks corresponding to individual buffer storage tanks, which is advantageous for securing a safe distance between processes and securing a facility area, and it is possible to secure the safety of workers due to the automated system.

In addition, in the buffer preparation and transfer system of the present invention, as the buffer preparation tank and the concentrated component tank are formed of a single-use (SU) disposable bag, corrosion (corrosion of a metal by an acid) caused by the use of a high-concentration buffer solution can be minimized, and a separate washing and sterilization process can be omitted, thereby further shortening the process time.

Further, the buffer preparation and transfer system of the present invention has a great advantage in that buffer quality is uniform compared to the related art, and the buffer solution can be prepared according to a desired recipe.

In the above, the present invention has been described with reference to exemplary embodiments, but the present invention is not limited to the described embodiments, and it is obvious to those skilled in the art or those of ordinary skill in the art that the present invention can be variously modified and changed without departing the spirit and scope of the present invention. Accordingly, such modifications or variations should not be individually understood from the technical spirit or point of view of the present invention, and the modified embodiments should belong to the claims of the present invention.

What is claimed is:

1. A buffer preparation and transfer system for a process of manufacturing an antibody pharmaceutical, comprising:

two or more concentrated component tanks configured to receive a concentrated component solution from a buffer preparation tank;

a first pipeline connected with a first discharge line along which the concentrated component solution is discharged from concentrated component tank;

one or more buffer storage tanks having concentrated component input lines each branched from the first pipeline and positioned in parallel;

a second pipeline connected with the second discharge line along which a buffer is discharged from each buffer storage tank;

a chromatograph connected with the second pipeline; and a control unit, wherein each of the two or more concentrated component tanks comprises different concentrated component solutions, respectively, wherein the different concentrated component solutions are different single component concentrated component solutions or multi-component concentrated component solutions comprising at least one different component of the components contained in a solution, wherein each of the one or more buffer storage tanks is connected to a line for injecting injectable water, and the buffer storage tank batch-conditions the injected concentrated component solution and the injectable water, wherein the control unit transfers the concentrated component solution to each buffer storage tank by adjusting the opening/closing of an opening/closing valve located on the first discharge line of each concentrated component tank or adjusting a flow rate with a flow rate-adjusting valve located on the concentrated component input line through which a concentrated component is introduced into each buffer storage tank by comparing values measured from one or more sensors selected from a weight sensor, a conductivity sensor, and a pH sensor provided in each buffer storage tank with a predetermined reference value, and wherein the buffer preparation tanks and concentrated component tanks are formed of single-use (SU) disposable bags, and the buffer storage tanks are formed of stainless steel (SS) material.

2. The system of claim 1, wherein the opening/closing valve is a pinch valve, and the flow rate-adjusting valve is a diaphragm valve.

3. The system of claim 1, wherein the chromatograph is one selected from an affinity chromatograph, an ion exchange chromatograph, a hydrophobic interaction chromatograph and a mixed-mode chromatograph, or a combination thereof.

4. The system of claim 1, wherein the buffer preparation and transfer system is applied to prepare and transfer a buffer for a process of purifying one or more antibody pharmaceuticals selected from the group consisting of abagovomab, abciximab, adalimumab, adecatumumab, alemtuzumab, altumomab, altumomab pentetate, anatumomab, anatumomab mafenatox, arcitumomab, atlizumab, basiliximab, bectumomab, ectumomab, belimumab, benralizumab, bevacizumab, brentuximab, canakinumab, capromab, capromab pendetide, catumaxomab, certolizumab, clivatuzumab tetraxetan, daclizumab, denosumab, eculizumab, edrecolomab, efalizumab, etaracizumab, ertumaxomab, fanolesomab, fontolizumab, gemtuzumab, girentuximab, golimumab, ibritumomab, igovomab, infliximab, ipilimumab, labetuzumab, mepolizumab, muromonab, muromonab-CD3, natalizumab, necitumumab, nimotuzumab, ofatumumab, omalizumab, oregovomab, palivizumab, panitumumab, ranibizumab, rituximab, satumomab, sulesomab, ibritumomab, ibritumomab tiuxetan, tocilizumab, tositumomab, trastuzumab, ustekinumab, visilizumab, votumumab, zalutumumab, brodalumab, anrukinzumab, bapineuzumab, dalotuzumab, demcizumab, ganitumab, inotuzumab, mavrilimumab, moxetumomab pasudotox, rilotumumab, sifalimumab, tanezumab, tralokinumab, tremelimumab, urelumab, adornase alfa, Rebif, becaplermin, alteplase, laronidase, alefacept, aflibercept, raxibacumab, darbepoetin alfa, becaplermin concentrate, interferon beta-1b, botulinum toxin type A, rasburicase, asparaginase, epoetin alfa, etanercept, agalsidase beta, interferon alfacon-1, interferon alfa-2a, anakinra, botulinum toxin type B, pegfilgrastim, oprelvekin, filgrastim, denileukin diftitox, peginterferon alfa-2a, aldesleukin, dornase alfa, interferon beta-1a, becaplermin, reteplase, interferon alfa-2, tenecteplase, drotrecogin alfa, rilonacept, romiplostim, methoxypolyethylene glycol-epoetin beta, a C1 esterase inhibitor, idursulfase, alglucosidase alfa, abatacept, galsulfase, palifermin and interferon gamma-1b.

\* \* \* \* \*